United States Patent [19]

Moore

[11] Plant 4,656

[45] Feb. 24, 1981

[54] MINIATURE ROSE PLANT

[76] Inventor: Ralph S. Moore, 2519 E. Noble Ave., Visalia, Calif. 93277

[21] Appl. No.: 111,843

[22] Filed: Jan. 14, 1980

[51] Int. Cl.[3] ..... A01H 5/00

[52] U.S. Cl. ..... Plt./8

[58] Field of Search ..... Plt./8

*Primary Examiner*—James R. Feyrer

[57] ABSTRACT

The subject of the present disclosure is a new and distinct variety of miniature rose plant characterized by the clear deep yellow color of the buds and flowers and by the profusion of bloom.

1 Drawing Figure

1

The present invention relates to a new and distinct variety of hardy, dwarf, bush type rose plant of the miniature class; the variety being primarily characterized—as to novelty—by clear deep yellow buds and flowers which in general color effect are similar to Golden Angel (miniature—U.S. Plant Pat. No. 4,028).

The variety is further characterized by:

An abundance of bloom with flowers usually borne singly (sometimes several) to the stem.

Sweet light fragrance.

A plant which is vigorous, of rounded somewhat upright shape with semi-glossy to matt, small foliage with pointed leaflets; the buds and flowers being similar in form and size to Calgold (miniature—U.S. Plant Pat. No. 4,230), but averaging more petals.

The plant, which has a normal height of 12–14 inches or more, can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at Sequoia Nursery located at Visalia, Calif., under conditions of careful control and observation as a seedling of Golden Angel (miniature—U.S. Plant Pat. No. 4,028) and presumably self pollenated with Golden Angel as no other varieties were growing nearby.

Subsequent to origination of the variety I successfully reproduced it, at Sequoia Nursery located as aforesaid, by budding as well as by cuttings; the reproductions having run true in all respects.

The color photograph illustrates the variety, including the foliage, buds and flowers.

Referring now specifically to the new and distinct variety of miniature rose plant, the following is a detailed description thereof in outline; all major color plate identifications being by reference to The British Colour Council Horticultural Colour Chart, except where common terms of color definition are employed.

Type: Hardy; dwarf; bushy; rounded; seedling; greenhouse; outdoors; cut flowers; garden decoration; potted plant.

Class: Miniature.

*Variety name.*—Shakespeare Festival.

Flowers borne: Usually singly or several together in loose spray or cluster on slender wirey stems.

Quantity of bloom: Abundant both outside and in greenhouse.

2

Bud:

*Peduncle.*—Medium to long length; slender but sturdy; erect; medium green, sometimes tinted bronze (outdoors); Hairs or tiny prickles—fairly numerous.

*Before calyx breaks, size.*—small. Form long; pointed with few or no foliaceous appendages on surface of bud; with foliaceous parts extending beyond the tip of the bud equal to one-half or more of its length. Color—medium green, occasionally tinted with bronze (outdoors).

*As calyx breaks, color.*—Deep yellow—near Lemon Yellow 4 or 4/1 with sometimes a light greenish cast. Opening: opens well in all weather.

Bloom:

*Size when fully open.*—Small, averaging about 35–40 mm (1½") or slightly larger.

*Petalage.*—Double—averaging about 35–40 petals, arranged regularly plus sometimes several small petaloids.

*Form.*—High centered at first, becoming more open, with petals reflexing loosely outward, and later at maturity, open and rolled loosely outward and downward. Open flowers show stamens.

Petals: Fairly thick; satiny on inside and on outside surface.

*Shape.*—Outside petals, broad lanceolate with rounded tip plus very small (short) acute tip; intermediate—broad lanceolate with rounded tip and very small (short) acute tip; inside—lanceolate with rounded or acute tip.

Color: Newly opened flower from a plant grown in unheated plastic greenhouse (Nov. 1979), Visalia, Calif.

*Outside petals.*—Outside surface—near Lemon Yellow 4/1 often tinted on basal ½ with deeper yellow. Inside surface near Lemon Yellow 4/1, shaded deeper yellow or greenish yellow near base.

*Intermediate petal.*—Outside surface—similar to outside petal. Inside surface—similar to outside petal.

*Inner petal.*—Outside surface—same as intermediate petal; inside surface—same as intermediate petal. General color effect; newly opened flowers—rich yellow. Three days open—color similar to newly opened flowers but less brilliant. Behavior—opens well in all weather. Spent petals drop off. Flower longevity (May 1979)— plant in pot 6–8 days or longer. Cut flowers at living room temperature 4–5 days or longer.

Reproductive organs:

*Stamens.*—Abundant, arranged regularly about pistils.

*Filaments.*—Varying length, fairly long, yellow.

*Anthers.*—Well formed; yellow.

*Pollen.*—Abundant.

*Pistils.*—Average number.

*Styles.*—Fairly even; medium to short length; bunched; color—yellowish.

*Ovaries.*—All enclosed in calyx.

*Hips.*—Fairly abundant; nearly round (apple shape); about 18–20 mm diameter.

*Sepals.*—Permanent; spear shaped; recurved against peduncle.

*Seed.*—Several per hip.

Foliage:

*Leaves.*—Compound of five (sometimes three) leaflets; fairly small; leathery; semi-glossy to matt.

*Leaflets.*—Shape: broad, nearly oval; apex acute; base rounded or rounded acute. Margin serrate. Color: medium to dark green; new growth—normal (medium) green. Rachis: medium strength; upper side may have several tiny short hairs, grooved; underside sparsely thorny with few or no tiny prickles. Stipules: medium long; narrow to medium width; medium length; narrow points which turn out usually at about 45°.

Growth:

*Habit.*—Dwarf; bushy; rounded; much branched.

*Growth.*—Free vigorous; internodes short.

*Canes.*—Medium; slender; sturdy.

*Main stems.*—color: medium green.

*Thorns.*—Average; slender; hooked downward; color: brown. Prickles—none. Hairs—none.

*Branches.*—Color: medium green. Thorns: moderate number; medium length; slender; hooked downward. Long oval base. Prickles: none. Hairs: none.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, bushy, rounded, much branched habit, substantially as illustrated and described, characterized by buds and flowers of a clear deep yellow color, being of a shade generally near Lemon Yellow 4 or 4/1, the bud and flower resembling the variety Golden Angel (Plant Pat. No. 4,028) in form and size but having less petals than Golden Angel and likewise resembling the variety Calgold (U.S. Plant Pat. No. 4,230) but averaging more petals; and further characterized by a plant of vigorous and compact growth habit, easy to propagate from cuttings or by budding, with an abundance of small to medium size semi-glossy to matt foliage and an abundance of flowers borne singly and in loose sprays or clusters of 3 to 5.

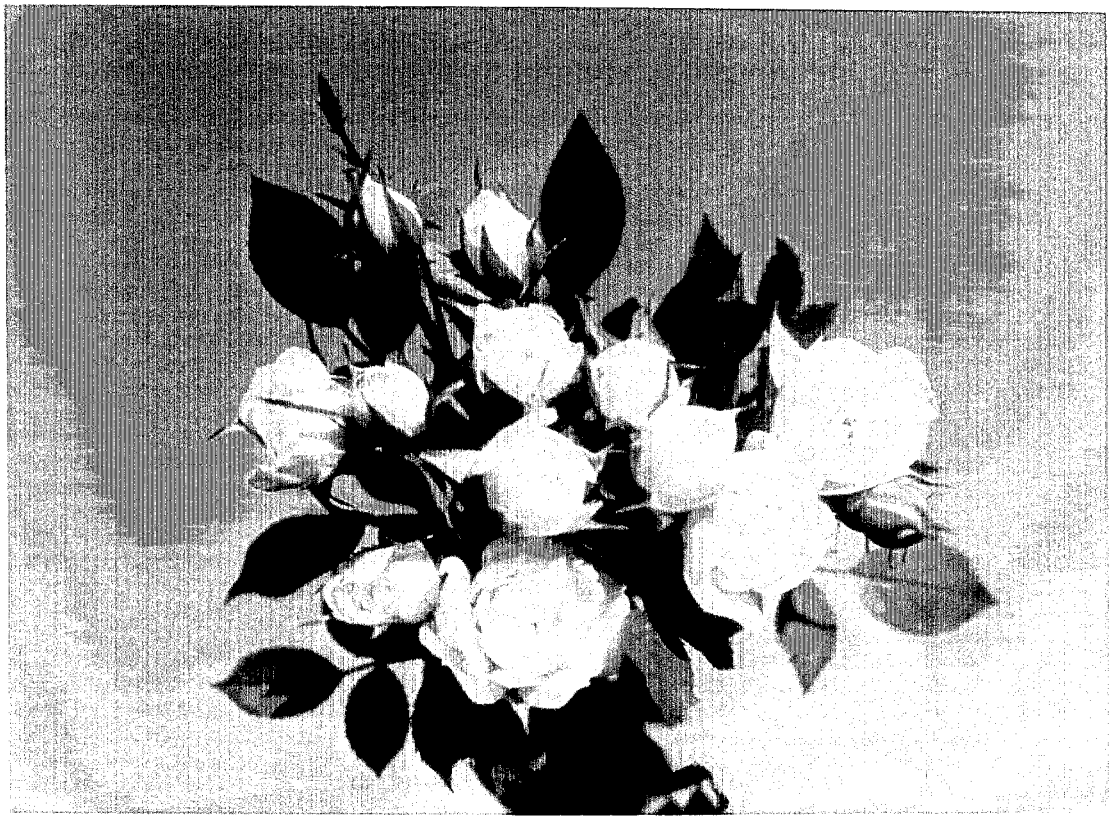

* * * * *